(12) United States Patent
Yokosuka et al.

(10) Patent No.: US 9,078,595 B2
(45) Date of Patent: Jul. 14, 2015

(54) OPHTHALMIC LASER TREATMENT APPARATUS

(75) Inventors: Hiroki Yokosuka, Aichi (JP); Tokio Ueno, Aichi (JP); Naho Murakami, Aichi (JP); Seiji Taki, Aichi (JP); Koichi Ito, Aichi (JP)

(73) Assignee: NIDEK CO., LTD., Aichi (JP)

( * ) Notice: Subject to any disclaimer, the term of this patent is extended or adjusted under 35 U.S.C. 154(b) by 100 days.

(21) Appl. No.: 13/609,876

(22) Filed: Sep. 11, 2012

(65) Prior Publication Data

US 2013/0261612 A1   Oct. 3, 2013

(30) Foreign Application Priority Data

Mar. 30, 2012   (JP) ................................ 2012-083095

(51) Int. Cl.
| | | |
|---|---|---|
| *A61B 18/18* | (2006.01) | |
| *A61B 3/10* | (2006.01) | |
| *A61B 3/12* | (2006.01) | |
| *H04N 5/232* | (2006.01) | |
| *A61F 9/008* | (2006.01) | |

(52) U.S. Cl.
CPC ... *A61B 3/10* (2013.01); *A61B 3/12* (2013.01); *A61F 9/008* (2013.01); *A61F 9/00821* (2013.01); *A61F 9/00804* (2013.01); *A61F 2009/0087* (2013.01); *A61F 2009/00851* (2013.01); *A61F 2009/00863* (2013.01); *A61F 2009/00872* (2013.01); *A61F 2009/00887* (2013.01); *H04N 5/23212* (2013.01)

(58) Field of Classification Search
CPC ................ H04N 5/23212; A61F 9/008; A61F 2009/00872; A61F 9/00821; A61F 9/00804; A61F 2009/00887; A61F 2009/0087

USPC .......................................................... 606/4–6
See application file for complete search history.

(56) References Cited

U.S. PATENT DOCUMENTS

| | | | |
|---|---|---|---|
| 6,932,807 B1 * | 8/2005 | Tomita et al. ................... 606/10 |
| 2006/0228011 A1 * | 10/2006 | Everett et al. ................. 382/128 |
| 2007/0129775 A1 | 6/2007 | Mordaunt et al. | |
| 2007/0216909 A1 * | 9/2007 | Everett et al. ................. 356/479 |
| 2010/0290007 A1 | 11/2010 | Van De Velde | |
| 2011/0184395 A1 * | 7/2011 | Schuele et al. ..................... 606/5 |
| 2011/0299034 A1 * | 12/2011 | Walsh et al. ................... 351/206 |

FOREIGN PATENT DOCUMENTS

| | | | |
|---|---|---|---|
| JP | 2009-514584 A | 4/2009 | |
| WO | 2007035855 A2 | 3/2007 | |

* cited by examiner

*Primary Examiner* — Lynsey Crandall
*Assistant Examiner* — Sebastian X Lukjan
(74) *Attorney, Agent, or Firm* — Rankin, Hill & Clark LLP

(57) ABSTRACT

An ophthalmic laser treatment apparatus includes a light interference optical unit, an irradiation unit, a luminance transition information detecting unit, a focused state detecting unit, and a guide unit. The light interference optical unit is configured to acquire a depth profile of a patient's eye tissue. The luminance transition information detecting unit is configured to control a first focus position adjusting unit to shift a focus position of a measurement light to acquire a depth profile in each focus position. The focused state detecting unit is configured to detect a focused state in the patient's eye tissue based on luminance transition information acquired by the luminance transition information detecting unit. The guide unit is configured to guide a focus position of a laser beam to be adjusted based on a result of detection of the focused state detecting unit.

20 Claims, 6 Drawing Sheets

OPHTHALMIC LASER TREATMENT APPARATUS

CROSS-REFERENCE TO RELATED APPLICATIONS

This application is based on Japan Patent Applications No. 2011-081289, filed on Mar. 31, 2011, and No. 2012-083095, filed on Mar. 30, 2012, in the Japan Patent Office, the disclosures of which are incorporated herein by reference in its entirety.

BACKGROUND

1. Technical Field

The present disclosure relates to an ophthalmic laser treatment apparatus to treat a patient's eye with irradiation of a laser light.

2. Related Art

A known ophthalmic laser treatment apparatus (see US 2007129775 and JP-T-2009-514564) treats an eye by irradiating a tissue of a patient's eye (such as a fundus) with a treatment laser light (laser beam). With this apparatus, an operator uses a slit lamp or similar equipment to observe a fundus. Once a portion of an eye to be treated is specified, the operator irradiates the portion of the eye with the laser light. The portion that is irradiated with the laser for treatment is thermally coagulated by energy of the laser light.

SUMMARY

An ophthalmic laser treatment apparatus is configured to irradiate a patient's eye with a treatment laser beam for treatment. The ophthalmic laser treatment apparatus includes a light interference optical unit, an irradiation unit, a luminance transition information detecting unit, a focused state detecting unit, and a guide unit. The light interference optical unit is configured to acquire a depth profile of the patient's eye tissue. The light interference optical unit includes: a measurement light source; a light splitter configured to split a light emitted from the measurement light source into a measurement light and a reference light where the measurement light is guided to and a reflected at the patient's eye; a first focus position adjusting unit configured to adjust a focus position of the measurement light in a patient's eye tissue; and a detector configured to detect an interference state between the measurement light and the reference light where the measurement light is reflected at the patient's eye. The irradiation unit includes a second focus position adjusting unit configured to adjust a focus position of a laser beam in the patient's eye tissue, and an irradiation optical system configured to irradiate the patient's eye tissue with the treatment laser beam emitted from the laser source. The luminance transition information detecting unit is configured to control the first focus position adjusting unit to shift the focus position of the measurement light so as to acquire a depth profile in each focus position. The luminance transition information detecting unit detects luminance transition information of the depth profile when the focus position is shifted. The focused state detecting unit is configured to detect a focused state in the patient's eye tissue based on the luminance transition information acquired by the luminance transition information detecting unit. The guide unit is configured to guide the focus position of the laser beam based on a detection result of the focused state detecting unit such that the focus position of the laser beam is adjusted to a targeted portion in the patient's eye tissue.

DETAILED DESCRIPTION

Figure 1:
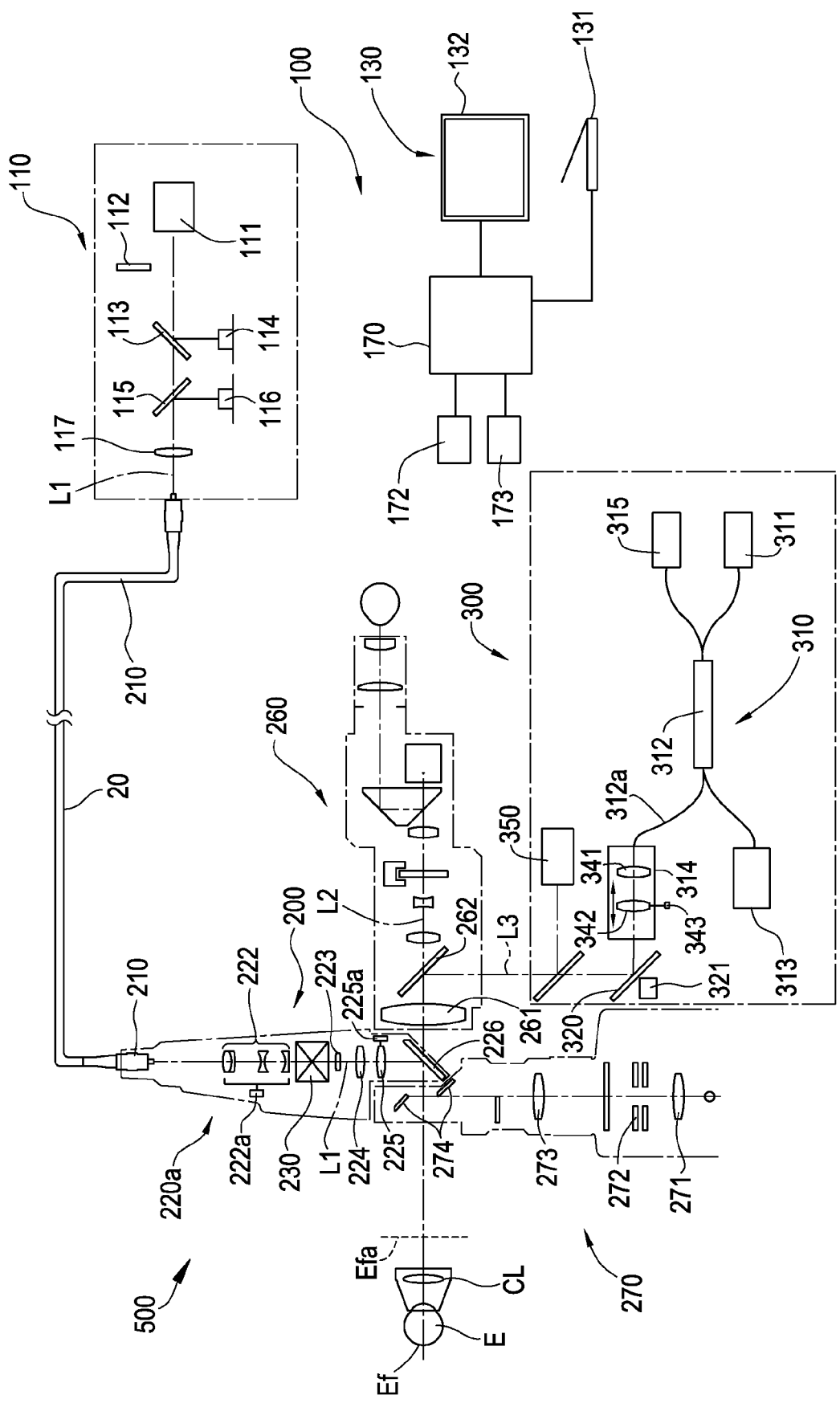
FIG. 1 is a schematic block diagram illustrating a configuration of an ophthalmic laser treatment apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmic laser treatment apparatus has difficulty in precisely focusing a laser spot of the treatment laser light on a specific portion (such as a specific layer in a retina). In view of this, for example, photocoagulation treatment for the fundus focuses the laser spot on a portion that is comparatively easy to view in the retina, for example, a pigmented layer. Then, the laser light is irradiated for the treatment. The irradiated laser light affects all retinal layers across the depth direction of the laser spot, thus the all retinal layers are non-selectively thermally coagulated. This causes a normal tissue (such as a normal layer of a photoreceptor cell) in the treated portion to lose its function.

An object of the present disclosure is to provide an ophthalmic laser treatment apparatus that selectively treats a specific portion of a patient's eye.

A description will be given on an embodiment according to the present disclosure below with reference to the accompanying drawings. FIG. 1 is a schematic block diagram illustrating a configuration of an ophthalmic laser treatment apparatus according to this embodiment. In this embodiment, the axial direction of an examinee's eye (eye E) denotes the Z direction, the horizontal direction denotes the X direction, and the vertical direction denotes the Y direction. Directions in a fundus surface may be denoted as the XY direction.

Overall Configuration of this Apparatus

A description will be given on the schematic configuration of this apparatus. This apparatus is a combination of an ophthalmic laser treatment apparatus and an optical coherence tomography unit (OCT unit). The ophthalmic laser treatment apparatus treats a fundus Ef of the patient's eye (examinee's eye) E by treatment laser light (laser beam) irradiation.

An ophthalmic laser treatment apparatus 500 includes a main body 100, a laser delivery part 200, and an optical coherence tomography unit 300 (hereinafter referred to as OCT unit). The main body 100 includes a laser source, a control unit, and an operating unit. The laser delivery part 200 includes an irradiation unit and a similar unit to irradiate the patient's eye E with the treatment laser light. The optical coherence tomography unit 300 acquires a tomographic image of the patient's eye E. The patient's eye E is brought in contact with a contact lens CL to optically cancel refractive power of a cornea so as to ensure observation on the fundus Ef of the patient's eye E. The contact lens CL has an anterior surface (at an operator side) that forms a fundus conjugate plane Efa as a conjugate plane of the fundus Ef. In this apparatus, a treatment laser light and a measurement light two-dimensionally scan the fundus conjugate plane Efa. The contact lens CL is held by the operator.

Main Body

The main body 100 includes a laser source unit 110, and an operating unit 130, and a control unit 170. The laser source unit 110 emits the treatment laser light (laser beam) and an aiming light (aiming beam) for sighting. Set-up and operation of the apparatus is performed by the operating unit 130. The control unit 170 integrally controls the whole apparatus. The laser source unit 110 includes a laser source 111, a safety shutter 112, a beam splitter 113, a power monitor 114, a dichroic mirror 115, an aiming light source 116, and a condenser lens 117. The laser source 111 emits a treatment laser light with an appropriate wavelength (here, from a medium wavelength to a long wavelength that are visible) for treatment of the patient's eye E. The safety shutter 112 is inserted in an optical axis L1 of the laser light to block irradiation of a laser light. The beam splitter 113 reflects a part of the laser light to the power monitor 114. The power monitor 114 allows monitoring of output of the laser light, which is reflected by the beam splitter 113. The dichroic mirror 115 aligns the aiming light in the same axis as the optical axis L1. The aiming light source 116 emits a laser light with a wavelength (here, visible wavelength) that allows the operator to view the position of the laser light spot. The laser light enters a fiber 210 after exiting the condenser lens 117. The operating unit 130 includes a foot switch 131 and a monitor 132 (details will be described later). The foot switch 131 inputs a signal that triggers the irradiation of the treatment laser light. The monitor 132 displays setting information of this apparatus, information on the patient's eye, and similar information. The monitor 132 has a touchscreen function. The touchscreen function allows the operator to input a setting signal and a specifying signal through the monitor 132. Although details will be described later, the control unit 170 integrally controls the whole apparatus. Additionally, the control unit 170 performs an analysis on the tomographic image, which is acquired by the OCT unit 300, an arithmetic operation of a focus position of a specified layer in the tomographic image, and a similar operation.

Laser Delivery Part

The laser delivery part 200 includes the fiber 210, an irradiation unit 220, which includes an irradiation optical system 220a, an observing unit 260, and an illumination unit 270. The fiber 210 guides the laser light emitted from the laser source unit. The irradiation optical system 220a irradiates the fundus Ef with the laser light emitted from the fiber 210 as a laser spot (hereinafter referred to as spot). The observing unit 260 includes an observing optical system for the operator to observe the fundus Ef. The illumination unit 270 projects an illuminating light to illuminate the fundus Ef.

The irradiation optical system 220a is a laser delivery system with a parfocal optical system that forms an image of the laser light emitted from an outgoing end surface of the fiber 210 on the fundus Ef (target surface). The irradiation unit 220 includes a lens 221, a zoom lens 222, a scanning unit 230, an image forming lens 223, an image forming optical system (lenses 224 and 225), and a mirror (final mirror) 226. The lens 221 relays the laser light emitted from the fiber 210 as a diffusion light. The zoom lens 222 is a variable magnification optical system that changes a size of the spot. The scanning unit 230 two-dimensionally scans the spot on the fundus Ef. The image forming lens 223 forms an image from the laser light that has passed through the scanning unit 230 in the middle of the optical path. The image forming optical system (lenses 224 and 225) forms an image of the spot at an intermediate image position, which is formed by the image forming lens 223, on the fundus Ef. The image forming optical system (lenses 224 and 225) includes a collimator lens 224, which collimates the laser light to a parallel light, and an objective lens (image forming lens) 225, which forms an image with the parallel light. The mirror 226 deflects the laser light to the patient's eye E.

The zoom lens 222 is held by a lens cam mechanism so as to move (slide) back and forth along the optical axis L1. The zoom lens 222 moves in accordance with rotation of a knob 222a by the operator. This consequently changes the spot size of the laser light.

Additionally, the objective lens 225 is held by the lens cam mechanism so as to move back and forth along the optical axis L1. The objective lens 225 (cam mechanism) is coupled to a driving part 225a with a potentiometer function. The objective lens 225 moves based on a command signal from the control unit 170. The movement of the objective lens 225 back and forth along the optical axis L1 moves a focus position of the spot in the depth direction (Z direction).

In this embodiment, the position of the objective lens 225 is adjusted based on an output signal from the OCT unit 300. The movement of the objective lens 225 is associated with movement of a diopter correction lens 342 in a measuring optical system 314 of the OCT unit 300. The movement of the diopter correction lens 342 changes the condensing position of the measurement light. The control unit 170 matches the condensing position of the measurement light with an image forming position of the treatment laser light. The objective lens 225 and the driving part 225a have a function to adjust a focus position (as second focus position adjusting means (unit)). Details will be described later.

The scanning unit 230 includes two galvanometer minors each having mutually orthogonal axis of rotation. The scanning unit 230 has a function to two-dimensionally deflect the laser light that has passed through the scanning unit 230, based on the command signal from the control unit 170.

The observing unit 260 is a binocular microscope, and includes an objective lens 261, a dichroic mirror (described later) 262, an operator protection filter 263, an erecting prism 264, and an eyepiece 265. The observing unit 260 has an observation optical path that is split corresponding to right and left eyes of the operator. Here, an optical axis of the observation optical path for the left eye is defined as an observed optical axis L2. The illumination unit 270 includes a lamp 271, which emits a visible light to be the illuminating light, a slit plate 272, which makes the illuminating light slit-shaped, a condenser lens 273, and a reflective mirror 274.

Optical Coherence Tomography Unit

The OCT (optical coherence tomography) unit, or the light interference optical unit 300 is mounted on the observing unit 260. The OCT unit 300 has a measurement light axis L3 that is adjusted by the dichroic minor 262. The adjustments made by the dichroic mirror 262 align the axes of the observed optical axis L2 of the observing unit 260 and the measurement light axis L3. The OCT unit 300 shares the objective lens 261 with the observing unit 260. The OCT unit 300, which captures a tomographic image of the fundus Ef of the patient's eye E, includes an interference optical system (OCT optical system) 310 and a frontal-view observing optical system 350. Typically, the dichroic mirror 262 has a characteristic that reflects an infrared light while transmitting a visible light.

OCT Optical System

The OCT optical system 310 irradiates the fundus with the measurement light. The OCT optical system 310 detects an interference state between the measurement light reflected by the fundus and the reference light at a light receiving device (detector 315). The OCT optical system 310 includes an optical scanner 320 to change an imaging position on the fundus Ef. The optical scanner 320 is an irradiation position changing unit that changes an irradiation position of the measurement light on the fundus Ef. The optical scanner 320 is coupled to the control unit 170. The control unit 170 controls operation of the optical scanner 320 based on a preset imaging position information, and acquires a tomographic image based on a light-receiving signal from the detector 315.

The OCT optical system 310 includes a configuration termed ophthalmic optical coherence tomography (OCT). In this embodiment, the OCT optical system 310 captures a tomographic image of the patient's eye before being irradiated with the treatment laser. The OCT optical system 310 splits the light (infrared light) emitted from a measurement light source 311 into the measurement light (specimen light) and the reference light using a coupler (light splitter) 312. The OCT optical system 310 guides the measurement light to the fundus Ef of the eye E using the measuring optical system 314 while guiding the reference light to the reference light optical system 313. The measurement light, which is reflected by the fundus Ef, and the reference light are combined as an interference light, which is received at the detector (light receiving device) 315.

The detector 315 detects the interference state between the measurement light and the reference light. In Fourier domain OCT, spectral intensity of the interference light is detected by the detector 315. The Fourier transformation on spectral intensity data allows acquisition of a depth profile (A-scan signal) in a predetermined range. For example, Spectral-domain OCT (SD-OCT), Swept-source OCT (SS-OCT), and Time-domain OCT (TD-OCT) may be used as well.

In SD-OCT, a low coherent light source (wideband light source) is used as the light source 311. The detector 315 includes a spectral optical system (spectrum meter) to disperse the interference light into respective frequency components (respective wavelength components). The spectrum meter includes, for example, a diffraction grating and a line sensor.

In SS-OCT, a wavelength scanning light source (variable wavelength light source) that temporally changes the outgoing wavelength at high speed is used as the light source 311. For example, a single light receiving device is used as the detector 315. The light source 311 includes, for example, a light source, a fiber ring resonator, and a wavelength selective filter. Typically, the wavelength selective filter may be, for example, a combination of the diffraction grating and the polygon mirror, and a filter with Fabry-Perot etalon.

The light emitted from the light source 311 is split into measurement light flux and reference light flux by the coupler 312. The measurement light flux is emitted to the air after passing through the optical fiber. The light flux is condensed on the fundus Ef through the optical scanner 320 and another optical member of the measuring optical system 314. Then, the light reflected at the fundus Ef returns to the optical fiber through a similar optical path.

The reference light optical system 313 generates the reference light, which is to be combined with a reflected light that is the measurement light reflected at the fundus Ef. The reference light optical system 313 may be a Michelson system or a Mach-Zehnder system. Typically, the reference light optical system 313 includes, for example, a catoptric system (such as, a reference mirror), which reflects the light from the coupler 312 to return this light to the coupler 312 again, and then guides the light to the detector 315. Additionally, the reference light optical system 313 includes a transmission optical system (such as, an optical fiber). The transmission optical system does not return the light from the coupler 312 but transmits and guides the light to the detector 315.

The reference light optical system 313 has a configuration that moves an optical member in a reference optical path to alter the difference in optical path length between the measurement light and the reference light. For example, the reference minor is moved in the optical axis direction. The configuration to change the difference in optical path length may be disposed in a measurement optical path of the measuring optical system 314.

The measuring optical system 314 includes a collimator lens 341, a diopter correction lens 342, and a driving part (actuator) 343. The collimator lens 341 collimates the measurement light from the optical fiber into a parallel light. The diopter correction lens 342 is a diopter correction optical system to correct the diopter scale of the patient's eye E. The driving part 343 moves the diopter correction lens 342. The driving part 343, which is coupled to the control unit 170, moves the diopter correction lens 342 back and forth along the optical axis L3. The diopter correction (movement of the focus position) has a range that is assumed to be approximately ±5 D in diopter. The command signal from the control unit 170 is assumed to continuously alter the diopter scale. The collimator lens 341 is disposed downstream to convert the measurement light flux emitted from the optical fiber into the parallel light. The lenses 341 and 342, the driving part 343, and the objective lens 261 have a focus position adjusting function (as first focus position adjusting means (unit)).

In this embodiment, the contact lens CL almost cancels the refractive power of the patient's eye. Additionally, movement of the laser delivery part 200 in the Z direction allows correction on the diopter scale of the patient's eye. Accordingly, the diopter correction lens 342 is used for condensing the measurement light in any position of the fundus tissue.

The measurement light is preferred to have a short focus depth (focus depth in the Z direction), so as to be condensed in a specific layer of the tomographic image. This consequently improves an S/N ratio when acquiring signal strength of the depth profile. Specifically, the measurement light is preferred to have a large light flux diameter on the objective lens 261, and high incidence NA (numerical aperture) of light to the fundus conjugate plane Efa is preferred. The patient's eye E is preferred to have a large pupil diameter that is, for example, approximately 2 to 6 mm. The light flux of the measurement light is thickened by, for example, a method where a lens with a comparatively long focus distance is used as the collimator lens 341 so as to enlarge the light flux diameter of the parallel light. A variable magnification optical system (not shown) to change the beam diameter of the parallel light is positioned between the collimator lens 341 of the measuring optical system 314 and the diopter correction lens 342. The variable magnification optical system may be, for example, a zoom optical system that moves a lens group along the optical axis, an optical system that inserts and removes the lens group in the optical path of the measuring optical system 314, or a similar optical system. For example, in the case that the tomographic image is captured, the parallel light is caused to have a small beam diameter. In the case that the diopter correction lens 342 is moved to acquire focus information, the parallel light is caused to have a large beam diameter.

The OCT unit 300 includes the optical scanner 320 to deflect the measurement light flux. The optical scanner 320 includes the two galvanometer minors each having mutually orthogonal axis of rotation. The optical scanner 320 has a function to two-dimensionally deflect a laser light that has passed through the scanning unit based on the command signal from the control unit 170. The optical scanner 320 scans the fundus Ef in the XY direction (traverse direction) with the measurement light. In this embodiment, the measurement light scans the fundus conjugate plane Efa. For example, the optical scanner 320 is operated in a straight line (such as the Y direction), and the depth profile acquired by the detector 315 is arranged in the straight line, thus acquiring the tomographic image (what is called, a B-scan).

This consequently changes the reflection (traveling) direction of the light flux emitted from the light source 311 so as to scan the fundus in any direction. This also changes the imaging position on the fundus Ef. The optical scanner 320 may have any other configuration insofar as the light is deflected. For example, an acousto-optic modulator (AOM) that alters the direction of travel (deflection) of the light may be used as the optical scanner 320, in addition to the reflective mirror (such as a galvanometer minor, a polygon mirror, and a resonant scanner). Refer to, for example, JP-A-2008-29467 for a detailed configuration of the OCT unit.

Frontal-View Observing Optical System

The frontal-view observing optical system 350 is provided to capture a frontal view image of the fundus Ef. The observing optical system 350 shares an axis parallel with the OCT optical system 310 with a dichroic mirror 351. The observing optical system 350 includes, for example, an optical scanner and a second light receiving device. The observing optical system 350 has a configuration of a so-called ophthalmic scanning laser ophthalmoscope (SLO) system. The optical scanner two-dimensionally scans the fundus (image plane) with the measurement light (such as an infrared light) transmitted from the light source. The second light receiving device receives light reflected from the fundus through a confocal aperture in a position substantially conjugated with the fundus. The configuration of the observing optical system 350 may have a configuration of a so-called fundus camera.

Control System

The control unit 170 performs image display control, image analysis, and input/output control of data in addition to integrated control and similar control of the whole apparatus. The control unit 170 integrally controls a function that guides a focus position of the laser beam to a targeted portion (treatment area) as described later. The control unit is coupled to a member of each constituent unit. Although not shown partially, the control unit 170 is coupled to the laser source 111, the safety shutter 112, the power monitor 114, the aiming light source 116, the scanning unit 230, the driving part 225a, the measurement light source 311, the reference light optical system 313, the detector 315, the driving part 343, the optical scanner 320, the frontal-view observing optical system 350, the foot switch 131, and the monitor 132. The control unit 170 also functions as an image processing part, which processes an acquired image, an image analyzer (analyzing unit), which analyzes the acquired image, and a similar unit. The control unit 170 includes a general CPU (Central Processing Unit) or a similar unit. The control unit 170 is coupled to a memory 171, which stores a processing program, various settings, an acquired image, and similar data. The control unit 170 is also coupled to a buzzer 173 as notifying means (notifier). The buzzer 173 notifies the operator of a situation with sound. In this situation, the aiming light is focused on the focus position when the treatment laser light is focused. The control unit 170 controls the optical scanner 320 based on acquired position information in the set tomographic image. Then, the control unit 170 determines a position in the XY direction to capture a tomographic image (B-scan image) of the fundus Ef. The control unit 170 controls the observing optical system 350 to acquire a frontal image.

This embodiment has a configuration such that the spot of the treatment laser light is condensed in a pinpoint position of the specific portion (specific layer) determined by the operator of the tomographic image. This pinpoint positioning selectively treats the specific portion, and reduces damage (especially, thermal damage) to peripheral portions (layers).

The control unit 170 controls the scanning unit 230, the laser source unit 110, and a similar unit based on irradiation position information (information to two-dimensionally arrange the spot) on the set fundus Ef. This consequently positions XY direction of the spot of the treatment laser light on the fundus Ef. The control unit 170 controls the driving part 225a to position the spot of the treatment laser light in the Z direction based on the focus information (described later). When the irradiation of the treatment laser light is aimed, the spot position of the treatment laser light is irradiated with the aiming light. For ease of explanation, the scanning unit 230 is assumed to be fixed on an origin (home position) on the XY plane below.

Focus Position Adjustment in the Irradiation Optical System

Figure 2:
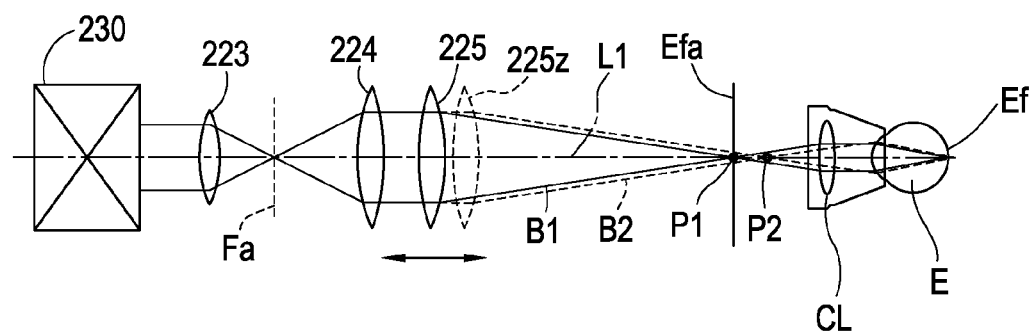
FIG. 2 is a schematic optical diagram illustrating an adjustment of a focus position of a spot in an irradiation optical system.

FIG. 2 is a schematic optical diagram illustrating an adjustment of the focus position of the spot in the irradiation optical system 220a. For ease of explanation, FIG. 2 omits the mirror 226 and illustrates the optical elements that appear after the scanning unit 230 (at the downstream side) in the center. The laser light that has passed through the scanning unit 230 uses the image forming lens 223 to form an image on an intermediate image plane Fa. The imaged laser light is converted into a parallel light by the collimator lens 224. This process forms an image of the laser light at a focus position P1 corresponding to a focus distance of the objective lens 225 (see light flux B1). The focus position P1 corresponds to the fundus conjugate plane Efa. Here, the objective lens 225 is assumed to travel forward (toward the patient's eye side) along the optical axis L1 of the laser light. An objective lens 225z, which is illustrated by dotted lines after the movement, forms an image with the parallel light from the collimator lens 224 at a focus position P2 of the objective lens 225z (similarly to the objective lens 225). Here, the spot position of the laser light travels forward corresponding to the movement distance of the objective lens 225z (see light flux B2). In the case that the objective lens 225 travels backward, the image forming position of the laser light travels backward. In view of this, the objective lens 225 moves in the Z direction along the optical axis. This process adjusts the focus position (spot position) of the laser light in the depth direction (Z direction). The image forming position of the laser light may be adjusted by moving the image forming lens 223 along the optical axis.

Diopter Correction in the OCT Optical System

Figure 3:
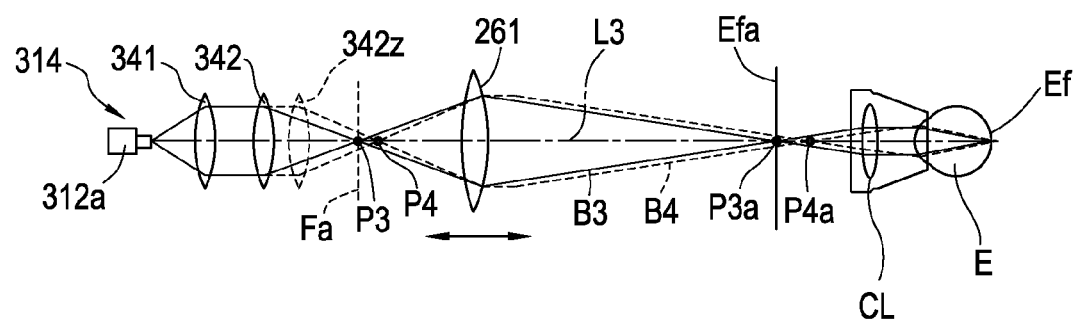
FIG. 3 is a schematic optical diagram illustrating a diopter correction in an OCT optical system.

FIG. 3 is a schematic optical diagram illustrating the diopter correction (adjustment of the condensing position of the measurement light) in the OCT optical system 310. For ease of explanation, FIG. 3 omits both the deflection of the optical path in the optical scanner 320 and the dichroic mirror 262, and illustrates optical elements that appear after the measuring optical system 314 in the center of the drawing. The light flux emitted from a fiber 312a of the fiber coupler 312 is collimated into a parallel light by the collimator lens 341, and then reaches the correction lens 342. The parallel light form an image at a focus position P3 corresponding to the focus distance of the correction lens 342. The light imaged at the focus position P3 is projected to a focus position P3a again by the objective lens 261 (see light flux B3). The focus position P3a corresponds to the fundus conjugate plane Efa. In this instance, the correction lens 342 is assumed to travel forward. Dotted lines illustrate a correction lens 342z after the movement. The correction lens 342z forms an image of the light flux, which is collimated into a parallel light by the collimator lens 341, at a focus position P4. The light flux imaged in the focus position P4 is projected to a focus position P4a again by the objective lens 261. Here, the focus position travels forward corresponding to the distance traveled by the correction lens 342z (see light flux B4). In the case that the objective lens 261 travels backward, the image forming position of the measurement light travels backward. Accordingly, the correction lens 342 travels in the Z direction along the optical axis. This adjusts the focus position of the measurement light in the depth direction (Z direction). This consequently corrects the diopter scale of the patient's eye E.

A description will be given on an operation in the apparatus with the above configuration. In general, the control unit 170 controls driving of the driving part 343 to shift the focus position of the measurement light. This process acquires a depth profile for each focus position, and detects luminance transition information on the depth profile when the focus position is shifted (see FIG. 7).

Figure 9:
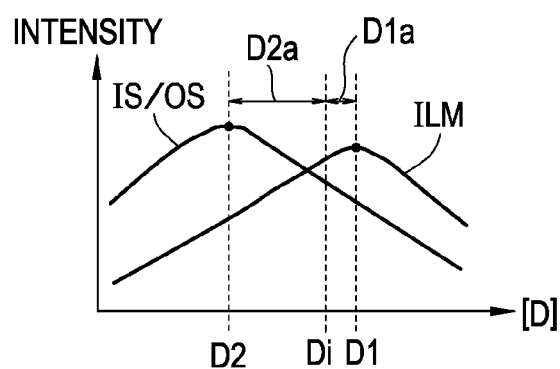
FIG. 9 is a graph showing a method for acquiring a focus position of a targeted portion from luminance transition information.
Figure 10:
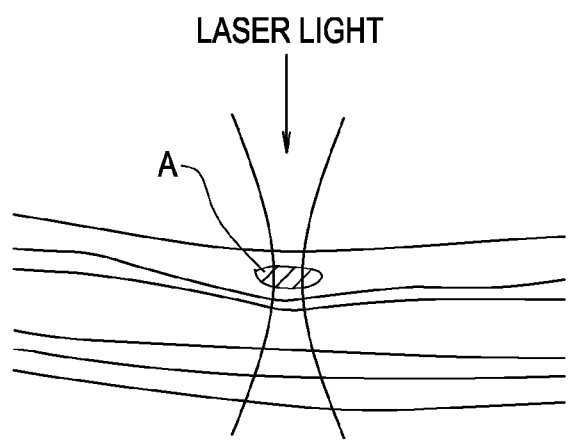
FIG. 10 is a diagram illustrating the focus position of the treatment laser light focused on an aneurysm.

Then, the control unit 170 detects the state of the focus in the patient's eye tissue based on the detected luminance transition information (see FIG. 9). The control unit 170 guides the laser beam to adjust the focus position of the laser beam to the targeted portion in the patient's eye tissue based on the detection results determined by the state of focus (see FIG. 10). In this embodiment, an interior portion of the patient's eye tissue is defined as inside of a layered predetermined portion (fundus) in an eyeball tissue.

Figure 5:
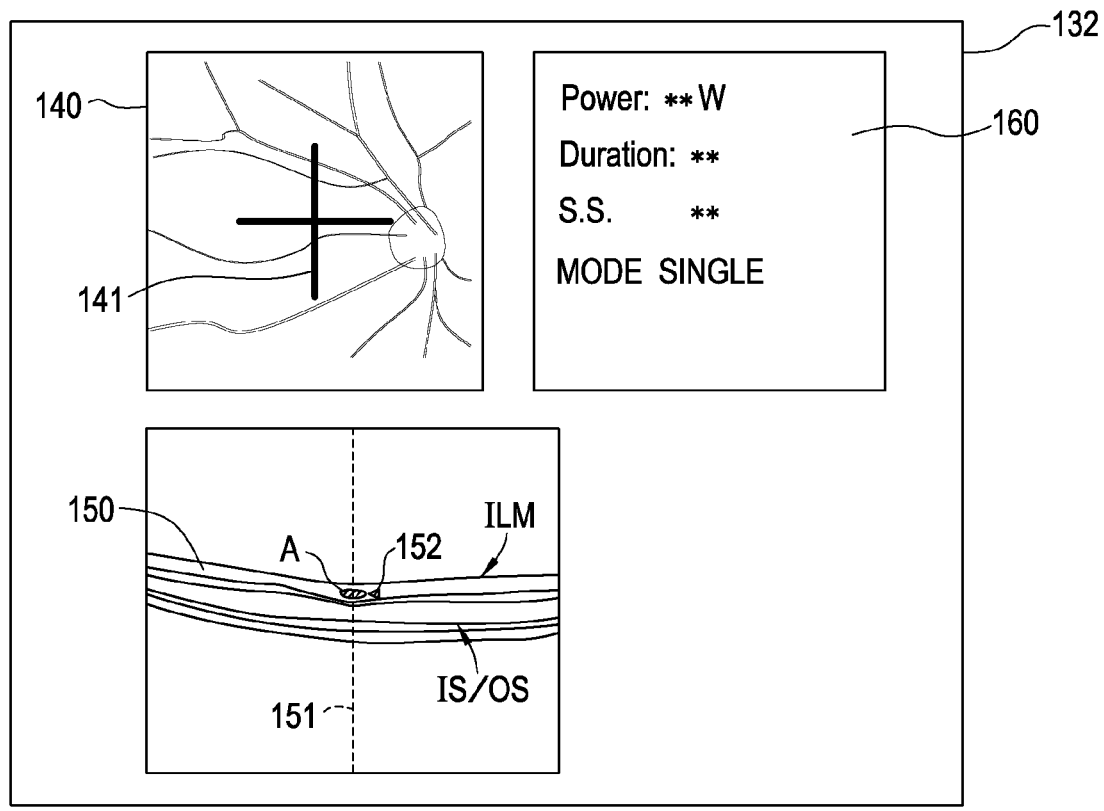
FIG. 5 is a diagram illustrating a display screen of a monitor.

In this case, a configuration that sets the targeted portion to be irradiated with the laser beam in the patient's eye tissue may be provided (see FIG. 5). Then, the control unit 170 acquires the focus position information corresponding to the set targeted portion based on the acquired luminance transition information (see FIGS. 8 and 9). Then, the control unit 170 controls driving of the driving part 225a to adjust the focus position toward a position corresponding to the acquired focus position information (see FIG. 10).

Figure 7:
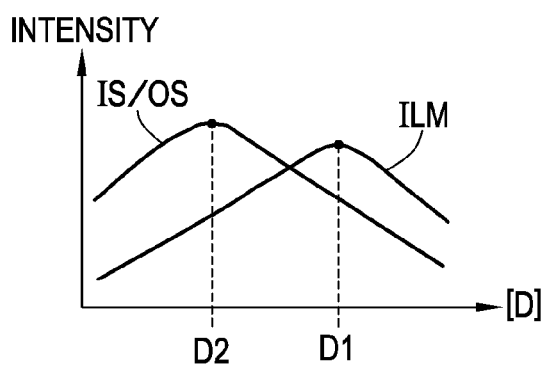
FIG. 7 is a graph showing plotted luminance values of an inner limiting membrane and an inner and outer segment layer of a retina in respective lens positions.

More preferably, the control unit 170 detects luminance transition information related to at least two characterizing portions in the patient's eye tissue (see IS/OS and ILM in FIG. 7). The control unit 170 acquires a focus position of the laser beam corresponding to the targeted portion in the patient's eye tissue from a positional relationship with the focus position corresponding to at least two characterizing portions (see FIGS. 8 and 9).

Procedure of Laser Treatment

Figure 4:
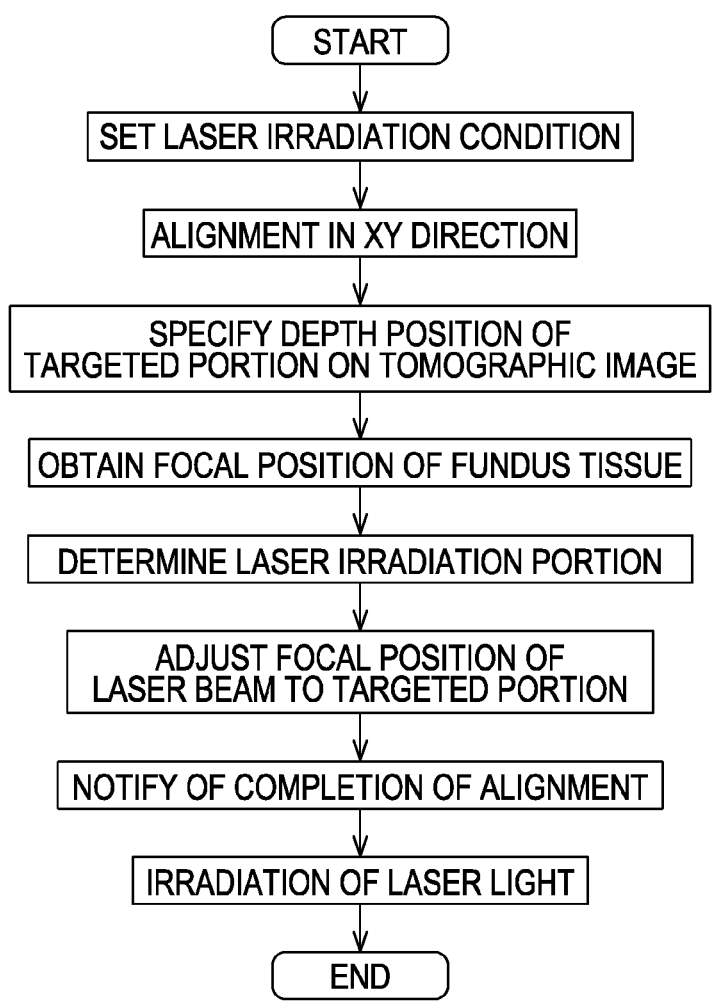
FIG. 4 is a flowchart explaining laser treatment.

A description will be given on a procedure of laser treatment using this apparatus 500. FIG. 4 is a flowchart explaining the procedure of the laser treatment. The fundus of the patient's eye is observed with the apparatus 500 to determine a laser irradiation portion, and perform treatment.

The operator sets the apparatus 500 prior to the treatment. The operator operates the knob 222a to set the spot size of the laser light, and operates an irradiation condition setting part 160 to set an irradiation condition of the laser and a similar parameter. It is preferred that the focus depth of treatment laser light be shallow so as to reduce influence of laser energy in the Z direction. The spot size is set to be small to make the NA (numerical aperture) of the treatment laser light larger. It is preferred that the spot size be comparable in size to a lesion area.

First, the operator brings the contact lens CL into contact with the patient's eye E, and then observes the fundus conjugate plane Efa through the observing unit 260 of the laser delivery part 200. At this time, the lesion area (here, an aneurysm, a blood vessel bump) on the fundus conjugate plane Efa is aligned (in the XY direction) in the center of the observation field. The aiming light is lighted to confirm the position of the laser spot. At this time, the control unit 170 controls the OCT unit 300 to display the frontal image and the tomographic image on the monitor 132. The operator performs fine adjustment of the alignment in the XY direction while examining the frontal image displayed on the monitor 132. This procedure aligns the aneurysm on an irradiation optical axis of the treatment laser.

Next, the operator uses the tomographic image displayed on the monitor to confirm the aneurysm in the Z direction. The operator touches (specifies) the position of the aneurysm on the tomographic image. The control unit 170 stores the touched position. The control unit 170 performs image processing on the tomographic image to acquire (specify the depth position of the targeted portion) a positional relationship (distance) between a superficial layer (surface) of the retina and the specified position. The control unit 170 controls the correction lens 342 of the OCT unit 300 based on a position specifying signal in the Z direction to acquire the depth profile. Then, the control unit 170 associates the position of the correction lens 342 with the position of the layer of the fundus based on the depth profile. The control unit 170 acquires a positional relationship between the aneurysm in the Z direction and the correction lens 342 so as to determine the irradiation position (in the Z direction) of the treatment laser light in the irradiation unit 220. For example, the control unit 170 acquires (determines a laser irradiation position) the distance from the superficial layer of the retina to the aneurysm in the Z direction.

Next, the control unit 170 moves the lens 225 such that the image forming position of the treatment laser light corresponds to the superficial layer of the retina based on the focus information. Then, the control unit 170 moves the lens 225 to align the image forming position of the treatment laser light with the position of the aneurysm in the Z direction. In other words, the image forming position of the treatment laser light is moved in the Z direction by the acquired distance from the superficial layer (alignment of the laser irradiation in the Z direction).

When alignment of the treatment laser light in the Z direction is completed, the control unit 170 notifies the operator of the completion of the alignment with the buzzer 173 or the like. The operator inputs a trigger signal of the laser the irradiation with the foot switch 131. The control unit 170 irradiates the patient's eye with the treatment laser light based on the trigger signal. The alignment of the treatment laser light in the Z direction may be performed based on the trigger signal of the foot switch 131. Then, the control unit 170 may perform irradiation of the treatment laser light after the completion of the alignment. This configuration precisely irradiates the lesion area (aneurysm) in the specific layer of the patient's eye fundus with the treatment laser light. This irradiation treatment reduces negative effects on tissues around the lesion area. Reduced damage to the photoreceptor cell in the back of the specific layer including the aneurysm results in the increased possibility of maintaining eyesight after the treatment (good prognosis after the treatment).

A description will be given below on detail of respective elements in the flowchart.

Monitor Display

Next, a display on the monitor will be described. FIG. 5 is a diagram illustrating a display screen of the monitor 132. The monitor 132 displays a frontal image 140, a tomographic image 150, and the irradiation condition setting part 160. The frontal image 140 is acquired with the frontal-view observing optical system 350. The tomographic image 150 is captured with the OCT optical system 310. The irradiation condition setting part 160 displays the setting the irradiation condition of the treatment laser light. For example, the control unit 170 acquires the tomographic image (OCT image) using image processing based on a light-receiving signal that is output from the detector 315 of the OCT optical system 310. The control unit 170 further acquires the frontal view image based on the light-receiving signal that is output from the light receiving device of the frontal-view observing optical system 350.

The acquired fundus image is output to the monitor 132 as a moving image. A memory 172 stores, for example, various information of imaging that includes image position information of the imaged tomographic images, the imaged frontal view images, and respective imaged tomographic images. The control unit 170 controls respective members of the OCT optical system 310 and the frontal-view observing optical system 350 based on an operation signal that is received from the monitor 132.

The frontal image 140 displays a cross mark 141. The cross mark 141 indicates a position of light sectioning in the tomographic image 150. The center of the cross mark 141 corresponds to the optical axis L1 of the treatment laser light and the optical axis L3 of the OCT measurement light. Here, the tomographic image is assumed to be acquired corresponding to the vertical line of the cross mark 141. The cross mark 141 may be temporarily eliminated from the screen by a switch (not shown).

The tomographic image 150 displays a line 151 and a mark 152. The line 151 indicates the optical axis (here, corresponding to the optical axis L1) when the treatment laser light is applied. The mark 152 specifies the condensing position of the laser light in the depth direction. Touching the screen of the tomographic image 150 by the operator moves the position of the mark 152. The monitor 132 functions as guide means (unit) for irradiation of the treatment laser light, and also functions as means of specifying the focus position. Here, the mark 152 is assumed to move along the line 151. Assume that an aneurysm A is in the layer of the fundus.

The irradiation condition setting part 160 displays an output setting part of the treatment laser light, an irradiation time (pulse width) setting part, a spot size display part, a mode setting part, and a similar part. The spot size is displayed as a numerical value based on the position of the zoom lens 222 read by the control unit 170. The mode setting part may set modes such as a pattern scan mode and a single mode. The pattern scan mode performs irradiation of the treatment laser light based on an irradiation pattern where a plurality of spots is arranged in a square-shaped pattern, a circular pattern, or a similar pattern. The single mode performs a single irradiation of the treatment laser light.

Acquiring the Luminance Transition Information

The control unit 170 acquires the luminance transition information at regular time intervals or when the position of mark 152 is moved.

The control unit 170 acquires the tomographic image, and then detects layer information of the fundus in the tomographic image with the image processing. Then, the OCT unit 300 analyzes the result of detection of the layer based on a predetermined image determining condition (determination criteria). In general, the control unit 170 changes the image forming position of the measurement light on the fundus (here, changed based on movement of the diopter correction lens 342). Further, the control unit 170 acquires luminance distribution in the depth profile (tomographic information only in the Z direction) by the A-scan in each image forming position. Then, the control unit 170 analyzes the luminance distribution acquired in each image forming position, and monitors an amplitude level of a signal corresponding to a predetermined retina layer for each of image forming positions. The amplitude level in the predetermined retina layer is detected with a signal processing technique (including an image processing technique) considering arrangement of each retina layer, the luminance value corresponding to each retina layer, and a similar condition.

Figure 6:
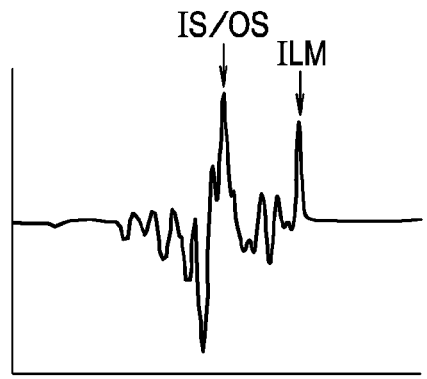
FIG. 6 is a graph showing a luminance distribution (signal strength in the Z direction) of an A-scan.

FIG. 6 is a graph showing a luminance distribution (signal strength in the Z direction) of an A-scan. The monitored retina layer includes an inner limiting membrane (ILM), which is a retinal superficial layer, an inner and outer segment layer (IS/OS), and a retinal pigment epithelium layer (RPE), each of which has a high peak in the luminance distribution.

This embodiment focuses on at least two layers (characterizing portions) that are comparatively distant from one another so as to be easily extracted by signal processing. In the case that attention is paid on at least two layers, a positional relationship (diopter scale (numerical value) corresponding to the positions) between these layers is acquired. Here, the ILM and the IS/OS are employed as specific examples. Here, the control unit 170 controls driving of the driving part 343 so as to move the correction lens 342 back and forth by predetermined steps. For example, the control unit 170 changes the position of the lens 342 from +5 D (diopter) to −5 D by 0.05 D steps. Accordingly, luminance distribution in 200 steps in the Z direction is acquired. The diopter scale of the patient's eye E is assumed to be preliminarily adjusted, that is, the focus position of the measurement light is arranged at the position of the fundus conjugate plane Efa.

FIG. 7 is a graph showing plotted luminance values of the ILM and the IS/OS in the respective lens positions. As shown in FIG. 7, as the lens 342 travels changing the condensing position in the fundus in the depth direction, the peak intensity of the ILM and the IS/OS varies. In the OCT optical system 310, in the case that luminance (reflected signal of the measurement light) of a layer is maximized, the reflected light (scattered light) from the layer that is the light flux between the correction lens 342 of the measuring optical system 314 and the collimator lens 341 is collimated into the parallel light, and is then condensed in the fiber 312a (see FIG. 3).

In FIG. 7, the luminance levels in layers are plotted in respective lens positions (information on variation in luminance is detected). This provides a monomodal plot as shown in FIG. 7. The ILM has a plot with a peak in a lens position corresponding to a diopter scale D1, while the IS/OS has a plot with a peak in a lens position corresponding to a diopter scale D2. The diopter scale D1 shows a pinpoint position where the measurement light (OCT optical system 310) is focused on the ILM, while the diopter scale D2 shows a pinpoint position where the measurement light is focused on the IS/OS. The luminance transition information indicates the focus position of the OCT unit 300 that is a position of the lens corresponding to the peak of the luminance in the specific layer (characterizing portion).

There is another layer (such as an inner plexiform layer, an inner nuclear layer, and an outer plexiform layer) between the ILM and the IS/OS. This layer may be specified by the relative positional relationship between the ILM and the IS/OS. For example, in the case that the specific layer is arranged in the intermediate position between the ILM and the IS/OS, the focus position (which is obtained by arithmetic mean of the diopter scale D1 and the diopter scale D2) corresponding to the intermediate position between the diopter scale D1 and the diopter scale D2 is arranged in the lens position corresponding to the specific layer. Thus, the lens position (diopter scale) corresponding to the relative positional relationship has a condition where the measurement light is focused on the specific layer. The diopter scale D1 and the diopter scale D2 thus obtained are stored in the memory 172 as focus information of the fundus.

Here, processing time for acquiring the focus information will be described. For example, scan speed of the A-scan is assumed to be 0.2 ms (5 kHz). Performing the A-scan with 10 D (±5 D) by 0.05 D steps is 200 steps at the speed of 40 ms (25 Hz). Accordingly, this allows update of the focus information to follow a frame rate (equal to or more than 10 frame/sec) capturing a moving image. Speckle noise may be reduced by adding the acquired data of the A-scan so as to improve extraction accuracy of the position in the layer such as the ILM. In the case that the diopter scale of the patient's eye E is adjusted to zero D, the diopter scale may be altered in either in a positive or negative direction.

Accordingly, the luminance transition information in the specific layer when the lens 342 is moved in the optical axis direction is acquired. This allows the measurement light to be condensed (focused) in the specific layer. For example, when focusing the measurement light on the ILM, the lens 342 is simply moved to a position corresponding to the diopter scale D1. Alternatively, when focusing the measurement light on the IS/OS, the lens 342 is simply moved to a position corresponding to the diopter scale D2.

In the case that the measurement light is focused on a tissue other than the ILM or the IS/OS (for example, aneurysm A in FIG. 8) as a target, a distance K1 and a distance K2 are calculated for example. The distance K1 is a distance from the ILM to a tissue PP (which is a tissue in the position of the aneurysm A). The distance K2 is a distance from the IS/OS to the tissue PP. In the luminance transition information as shown in FIG. 9, in the case that a distance D1$a$ is assumed to be a distance from the diopter scale D1 while a distance D2$a$ is assumed to be a distance from the diopter scale D2, a focus position Di where K1/K2 is equal to D1$a$/D2$a$ is obtained. Then, moving the lens 342 to a position corresponding to the focus position Di allows the measurement light to be focused on the tissue PP.

Use of this information allows acquisition of the luminance transition information in the specific layer in the case that the lens 342 is moved in the optical axis direction. This allows the treatment laser light to be condensed (focused) at the specific layer. In this case, the moving position of the lens 225 is associated (for example, diopter conversion) with the moving position (movement control) of the lens 342 such that the focus position of the laser light with respect to the fundus Ef is set to be in a position corresponding to the focus position of the measurement light adjusted by the lens 342. Accordingly, the irradiation optical system 220$a$ is associated with the OCT optical system 310 regarding the focus position.

In this case, for example, when focusing the laser light on the ILM, the lens 225 is simply moved to a position corresponding to the diopter scale D1. When focusing the laser light on the IS/OS, the lens 225 is simply moved to a position corresponding to the diopter scale D2.

In the case that the laser is focused on a tissue other than the ILM or the IS/OS (see the tissue PP in FIG. 8 for example) as the target, the distance K1 and the distance K2 are acquired for example. The distance K1 is a distance from the ILM to the tissue PP. The distance K2 is a distance from the IS/OS to the tissue PP. In the luminance transition information as shown in FIG. 9, in the case that the distance D1$a$ is assumed to be a distance from the diopter scale D1 while the distance D2$a$ is assumed to be a distance from the diopter scale D2, the focus position Di where K1/K2 is equal to D1$a$/D2$a$ is obtained. Then, moving the lens 225 to a position corresponding to the focus position Di focuses the laser light on the tissue PP.

Acquisition of Pinpoint Focus Information and Pinpoint Focusing

Figure 8:
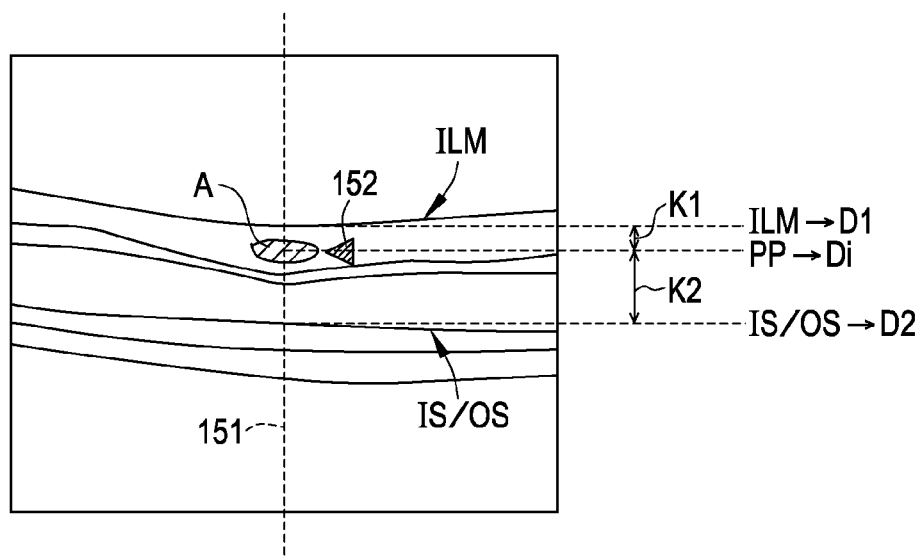
FIG. 8 is a schematic diagram illustrating a specific example where a focus position of a treatment laser light is precisely adjusted.

FIG. 8 is a schematic diagram illustrating a specific example where the focus position of the treatment laser light is precisely adjusted.

First, the control unit 170 controls the driving part 225$a$ based on the luminance transition information (see FIG. 7) acquired as described above as an initial setting. Then, the control unit 170 moves the lens 225 to a position corresponding to the diopter scale D1 in the OCT optical system 310. This allows the focus position of the irradiation optical system 220$a$ to be aligned on the ILM of the fundus Ef. The control unit 170 displays the mark 152 superimposed on the display position. The display position corresponds to the ILM on the tomographic image 150 at an early stage.

Here, the operator examines the tomographic image 150 to determine the layer to be treated. Here, the operator confirms the aneurysm A on the tomographic image 150, touches the position of the aneurysm A, and then determines the position of the mark 152. The mark 152 is displayed in the position of the aneurysm A as illustrated in FIG. 5.

FIG. 8 is a diagram illustrating an example where the focused aneurysm A is detected. The control unit 170 analyzes the acquired tomographic image and performs image processing to detect each layer. At this time, at least the ILM and the IS/OS are detected.

Then, the control unit 170 obtains the distance K1 and the distance K2. The distance K1 is a distance from the aneurysm A, which is specified by the mark 152, to the ILM. The distance K2 is a distance from the aneurysm A, which is specified by the mark 152, to the IS/OS. This obtains a relative positional relationship between the targeted portion (aneurysm A), which is specified by the operator, and the two layers (ILM and IS/OS) of the fundus.

Next, the control unit 170 uses the luminance transition information, which is stored in the memory 171 as described above (see FIG. 9), to acquire the focus position Di corresponding to the aneurysm A. Then, the distance D1$a$ is assumed to be a distance from the diopter scale D1 to the focus position D1, while the distance D2$a$ is assumed to be a distance from the diopter scale D2 to the focus position Di. In this case, the control unit 170 acquires the focus position Di where K1/K2 is equal to D1$a$/D2$a$. That is, the control unit 170 acquires the focus position corresponding to the aneurysm A where following two positional relationships are equivalent. One is a positional relationship between the aneurysm A specified by the operator and the two layers of the fundus, and the second is a positional relationship between the focus position Di corresponding to the aneurysm A and the focus positions (diopter scales D1 and D2) corresponding to the two layers.

Then, the control unit 170 controls driving of the driving part 225a, and moves the lens 225 to a position corresponding to the focus position Di. In this embodiment, the focus position of the irradiation optical system 220a is focused on the ILM as an initial setting. Accordingly, the control unit 170 calculates a deviation amount between the focus position Di corresponding to the aneurysm A (tissue PP) and the focus position corresponding to the ILM. The control unit 170 moves the lens 225 forward by this deviation amount. This allows the focus position of the irradiation optical system 220a to be aligned on the aneurysm A (see FIG. 10).

As described above, in the case that the focus of the irradiation optical system 220a is focused on the aneurysm A, the control unit 170 notifies the operator of completion of focusing with the sound of the buzzer 173. Then, when the operator pushes the foot switch 131, the control unit 170 controls the laser source unit 110 to irradiate the fundus Ef (fundus image plane Efa) with the treatment laser light. The aneurysm A of the focused layer in the fundus Ef is selectively affected by the treatment laser light, thus being coagulated. At this time, a thermal effect on other layers is reduced.

This allows a selective treatment of the targeted portion of the patient's eye E. This reduces damage on the periphery of the specific portion with the aneurysm, for example, the photoreceptor cell in the back of the layer. This process enhances the possibility of maintaining eyesight after the treatment (good prognosis after the treatment).

While in the scanning unit 230 does not scan with the laser light in the above description, the scanning unit 230 is not limited to this configuration. For example, the scanning unit 230 may sequentially perform irradiation of the treatment laser light along the specific layer of the tomographic image (B-scan) that is acquired by the OCT optical system 310.

In this case, for example, the control unit 170 acquires a relationship between the moving position of the lens 342 and the focus position of the measurement light on the fundus for each scan position (XY position). Then, the control unit 170 detects the respective focus position corresponding to the targeted portion regarding a plurality of irradiation positions (which are acquired from the irradiation position of the aiming light and the scan position by the scanning unit 230, for example) to be irradiated with the treatment laser light. While the treatment laser light scans, the control unit 170 controls driving of the driving part 225a for each irradiation position such that the lens 225 is moved to the focus position corresponding to the targeted portion.

The above method may also be employed in the case that the treatment laser light two-dimensionally scans the fundus. Here, the control unit 170 also controls the OCT optical system 310 to two-dimensionally scan the fundus Ef with the measurement light. Then, the control unit 170 may acquire the relationship between the moving position of the lens 342 and the focus position of the measurement light on the fundus Ef, for each scan position (XY position). In this case, for example, the control unit 170 three-dimensionally acquires the tomographic image in each position of the lens 342. In this case, scanning with the measurement light may employ a raster scan, a multi-line scan, or a radial scan.

Then, the control unit 170 detects the respective focus positions corresponding to the targeted portions that are related to a plurality of irradiation positions (which are acquired from the irradiation position of the aiming light for example) to be irradiated with the treatment laser light. During the laser light scans, the control unit 170 controls the driving part 225a to move the lens 225 to the focus position corresponding to the targeted portion for each irradiation position.

In the case that the treatment laser light scans as described above, the control unit 170 does not need to detect the respective focus positions corresponding to the targeted portions that are related to the irradiation positions. The control unit 170 may detect a focus position corresponding to a targeted portion that is related to a certain irradiation position. In this case, the lens 225 is adjusted such that the focus position related to the certain irradiation position is diverted to other irradiation positions.

The control unit 170 may acquire the irradiation position information of the aiming light when the treatment laser light is applied, so as to acquire the focus position corresponding to the targeted portion that is related to the irradiation position of the aiming light. The control unit 170 may acquire the focus position of the targeted portion from the scan position (angle information of the galvanometer mirror) in the scanning unit 230. Then, the control unit 170 irradiates the position corresponding to the aiming light with the laser light while adjusting the position of the lens 225 based on the acquired focus position when the foot switch 131 is pushed.

While the operator specifies the targeted portion on the tomographic image 150 so as to set the focus position of the laser beam in the above description, the configuration is not limited to this. This configuration may allow the operator to adjust the focus position of the laser beam while examining the tomographic image. For example, the guide mark is displayed in the position on the tomographic image corresponding to the focus position of the laser beam. Then, the operator moves the mark in accordance with the operation of a focus knob (knob to move the lens 225).

While the operator examines the tomographic image to determine the pinpoint focus position in the above description, the configuration is not limited to this. The control unit 170 analyzes (determines) the targeted portion based on the result of detection of the layer in the tomographic image. The control unit 170 may move the lens 342 to acquire the position of the layer in the fundus, and then determine the pinpoint focus position corresponding to the targeted portion in the fundus tissue.

For example, the operator determines the treatment area (alignment in the XY direction) while examining the fundus Ef of the patient's eye E with the observing unit 260. Then, when the operator pushes the foot switch 131, the control unit 170 controls the OCT unit 300 to acquire the focus information. Then, the control unit 170 detects the layer in the tomographic image (or depth profile). The control unit 170 analyzes the state of the layer to determine the targeted portion (the abnormal portion). The control unit 170 determines the pinpoint focus position based on the determination result, and controls the driving part 225a. The control unit 170 notifies the operator of completion of pinpoint focusing with the buzzer 173. Then, the control unit 170 irradiates the targeted portion with the treatment laser light when the operator pushes the foot switch 131 again. Alternatively, the irradiation of the treatment laser light may be performed automatically by the control unit 170.

While the OCT optical system 310 and the irradiation optical system 220a are separate optical systems in the above description, these optical systems may be combined. For example, the scanning unit 230 of the irradiation optical system 220a is combined with the optical scanner 320. The lens that adjusts the condensing position of the measurement light in the OCT unit may be combined with the lens that adjusts the image forming position of the treatment laser light (integration of the first focus position adjusting means and the second focus position adjusting means). Accordingly, the OCT unit acquires the position of the layer in the fundus based on the lens position. This acquires the image forming position of the treatment laser light.

While the configuration acquires the lens positions corresponding to the focus positions of the two characterizing portions based on the luminance transition information so as to acquire the focus information in the above description, the configuration is not limited to this. The characterizing portion may be one. For example, the configuration may acquire the lens position where the ILM is in focus, and move the focus position of the laser beam from the ILM in the Z direction so as to perform the laser irradiation. In this case, the amount of movement of the lens 225 and the depth position of the fundus tissue may be determined considering the magnification of the contact lens CL and the refractive index of the patient's eye (approximately constant).

While the configuration adjusts the focus position of the laser beam by movement of the objective lens 225 along the optical axis in the above description, the configuration is not limited to this. Any configuration is possible insofar as the focus position of the laser beam is adjusted in the Z direction. For example, the configuration may move the laser delivery part 200 or the irradiation unit 220 back and forth.

The aforementioned configuration may further include a tracking function. For example, the control unit 170 extracts a feature point (such as an optic disc) from the fundus image (such as an SLO image) of the patient's eye acquired by the OCT unit 300. Then, the control unit 170 acquires the position of the feature point in real time, and then controls the optical scanner 320 based on the position information so as to place the measurement light at a constant position on the targeted portion. This acquires the tomographic image and the depth profile while following (tracking) fine involuntary movement during fixation of the patient's eye. This configuration may further include a fixation optical system that presents a fixation light to the patient's eye so as to fixate the patient's eye to the OCT unit 300. This reduces influence by the fine involuntary movement during fixation of the patient's eye during observation and treatment. In addition, this easily guides a visual line of the patient's eye, thus smoothly determining the irradiation position of the laser.

The configuration may further include a tracking function in the Z direction. For example, the configuration performs real-time monitoring of the depth profile that is acquired by the OCT unit 300. This monitoring detects an amount of displacement of the characterizing portion such as the ILM in the Z direction with respect to a predetermined position in the depth direction. Subsequently, the configuration moves the objective lens 225 so as to correspond to the amount of displacement so that the image forming position of the treatment laser light is adjusted in the Z direction (which is a tracking in the Z direction).

The configuration may adjust the difference in the optical path length between the measurement light and the reference light so as to position the characterizing portion such as the ILM in a predetermined position with respect to the predetermined position in the depth direction for acquiring the tomographic image. This process reduces sensitivity unevenness of the depth profile.

While the treatment laser light is a continuous-wave laser light to perform coagulation or similar procedures in the above description, the treatment laser light is not limited to this. A pulse laser to mechanically break (or excise) the targeted portion may be used as the light source.

While the configuration treats the fundus of the patient's eye in the above description, the configuration may treat another portion of the patient's eye. Any portion of a layered tissue of the eyeball is applicable as a predetermined portion. For example, the portion may be a cornea, a crystalline lens, or a similar portion. In the above description, the diopter correction lens 242 acquires the focus information of the fundus. However, in the case where the patient's eye tissue is not the fundus, the configuration may employ an optical element (lens and minor) to adjust the condensing position of the measurement light in the OCT unit 300, instead of the diopter correction lens.

Various modifications and variations are possible with ingenuity by those skilled in the art. These configurations are included within the scope of the present disclosure.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmic laser treatment apparatus for irradiating a patient's eye with a treatment laser beam for treatment, the ophthalmic laser treatment apparatus comprising:
   a light interference optical unit configured to acquire a depth profile of a patient's eye tissue, the light interference optical unit including: a measurement light source; a light splitter configured to split a light emitted from the measurement light source into a measurement light and a reference light, the measurement light being guided to and reflected at the patient's eye; a first focus position adjusting unit configured to adjust a focus position of the measurement light in the patient's eye tissue; and a detector configured to detect an interference state between the measurement light and the reference light, the measurement light being reflected at the patient's eye;
   an irradiation unit including: a second focus position adjusting unit configured to adjust a focus position of a laser beam in the patient's eye tissue; and an irradiation optical system configured to irradiate the patient's eye tissue with the treatment laser beam, the treatment laser beam being emitted from a laser source;
   a luminance transition information detecting unit configured to control the first focus position adjusting unit to shift the focus position of the measurement light so as to acquire a depth profile in each focus position, the luminance transition information detecting unit detecting luminance transition information of the depth profile when the focus position is shifted;
   a focused state detecting unit configured to detect a focused state in the patient's eye tissue based on the luminance transition information, the luminance transition information being acquired by the luminance transition information detecting unit; and
   a guide unit configured to guide the focus position of the laser beam based on a result of detection of the focused state detecting unit such that the focus position of the laser beam is adjusted to a targeted portion in the patient's eye tissue, wherein the luminance transition information detecting unit is configured to detect luminance transition information relating to at least two characterizing portions in the patient's eye tissue;

the focused state detecting unit is configured to acquire the focused state based on a positional relationship between the two characterizing portions; and the luminance transition information detecting unit is configured to control the first focus position adjusting unit to shift the focus position of the measurement light such that a luminance level of reflected measurement light when the focus position is shifted to the characterizing portion is greater than a luminance level of reflected measurement light when the focus position is shifted to positions that are other than the characterizing portions.

2. The ophthalmic laser treatment apparatus according to claim 1, wherein
the guide unit controls the first focus position adjusting unit such that the focus position of the laser beam is adjusted to the targeted portion in the patient's eye tissue.

3. The ophthalmic laser treatment apparatus according to claim 1, further comprising:
a setting unit configured to set the targeted portion in the patient's eye tissue, the targeted portion being irradiated with the laser beam, wherein
the focused state detecting unit is configured to acquire focus position information based on the luminance transition information, the luminance transition information being acquired by the luminance transition information detecting unit, the focus position information corresponding to the targeted portion set by the setting unit, and
the guide unit is configured to control the second focus position adjusting unit so as to adjust the focus position toward a position corresponding to the focus position information.

4. The ophthalmic laser treatment apparatus according to claim 1, further comprising:
a display configured to display the depth profile acquired by the light interference optical unit as a tomographic image, wherein
the guide unit is configured to display a mark on the display based on the result of detection the focused state detecting unit, the mark being indicative of the focus position of the laser beam in the tomographic image.

5. The ophthalmic laser treatment apparatus according to claim 4, wherein
the setting unit is configured to set the targeted portion to the tomographic image on the display.

6. The ophthalmic laser treatment apparatus according to claim 1, further comprising:
an analyzing unit configured to extract a treatment area based on the depth profile, the depth profile being acquired by the light interference optical unit, wherein
the focused state detecting unit is configured to acquire focus position information based on the luminance transition information, the focus position information defining the treatment area as the targeted portion, the treatment area being extracted by the analyzing unit.

7. The ophthalmic laser treatment apparatus according to claim 1, further comprising:
a notifier configured to provide a notification that the focus position of the laser beam is adjusted to the targeted portion by the guide unit.

8. The ophthalmic laser treatment apparatus according to claim 1, wherein a relationship between the focus positions adjusted by the first focus position adjusting unit is associated with a relationship between the focus positions adjusted by the second focus position adjusting unit such that the focus position acquired by the focused state detecting unit is associated with the focus position of the laser beam.

9. The ophthalmic laser treatment apparatus according to claim 1, wherein
an interior portion of the patient's eye tissue is defined as inside of a layered predetermined portion in an eyeball tissue.

10. The ophthalmic laser treatment apparatus according to claim 9, wherein
the predetermined portion is any one of a cornea, a crystalline lens, and a fundus.

11. The ophthalmic laser treatment apparatus according to claim 10, wherein
the predetermined portion is a fundus, and
the targeted portion to be irradiated is one of a blood vessel and a blood vessel bump of the fundus.

12. An ophthalmic laser treatment method of irradiating a patient's eye with a treatment laser beam for treatment, the ophthalmic laser treatment method comprising: acquiring a depth profile of a patient's eye tissue using: a measurement light source; a light splitter configured to split a light emitted from the measurement light source into a measurement light and a reference light, the measurement light being guided to and reflected at the patient's eye; a first focus position adjusting unit configured to adjust a focus position of the measurement light in the patient's eye tissue; and a detector configured to detect an interference state between the measurement light and the reference light, the measurement light being reflected at the patient's eye; irradiating the patient's eye tissue with the treatment laser beam emitted from a laser source using a second focus position adjusting unit configured to adjust a focus position of a laser beam in the patient's eye tissue;
shifting the focus position of the measurement light to detect luminance transition information of the depth profile relating to at least two characterizing portions in the patient's eye tissue such that a luminance level of reflected measurement light when the focus position is shifted to the characterizing portion is greater than a luminance level of reflected measurement light when the focus position is shifted to positions that are other than the characterizing portions so as to acquire a depth profile in each focus position;
detecting a focused state in the patient's eye tissue based on the luminance transition information, the luminance transition information being acquired by the detecting luminance transition information; and
guiding the focus position of the laser beam based on a positional relationship between the two characterizing portions such that the focus position of the laser beam is adjusted to a targeted portion in the patient's eye tissue.

13. The ophthalmic laser treatment apparatus according to claim 1, wherein the focused state detecting unit is configured such that the luminance transition information is calculated by the luminance transition information detecting unit based on a depth profile at each focus position.

14. The ophthalmic laser treatment apparatus according to claim 1, wherein the focused state detecting unit is configured to detect a focused state with respect to a targeted portion in a tissue.

15. The method of claim 12, further comprising the action of calculating the luminance transition information based on a depth profile at each focus position.

16. The method of claim 12, further comprising the action of detecting a focused state with respect to a targeted portion in a tissue.

17. The ophthalmic laser treatment apparatus according to claim 1, wherein
- the focused state detecting unit is configured to detect at least two characterizing portions comprising first and second characterizing portions in the luminance transition information of the depth profile of the patient's eye tissue and to acquire a first distance from the first characterizing portion to the targeted position and a second distance from the second characterizing portion to the targeted position; and
- the guide unit is configured to guide the focus position of the laser beam based on a ratio of the first distance to the second distance.

18. The ophthalmic laser treatment apparatus according to claim 1, wherein
- the light interference optical unit is configured to acquire a depth profile of a fundus of the patient's eye;
- the irradiation optical system is configured to irradiate the fundus of the patient's eye with the treatment laser beam;
- the luminance transition information detecting unit is configured to detect luminance transition information of the depth profile of the fundus of the patient's eye;
- the focused state detecting unit is configured to detect at least two characterizing portions comprising first and second characterizing portions in the luminance transition information of the depth profile of the fundus of the patient's eye and to acquire a first distance from the first characterizing portion to the targeted position and a second distance from the second characterizing portion to the targeted position; and
- the guide unit is configured to guide the focus position of the laser beam within the fundus based on a ratio of the first distance to the second distance.

19. The ophthalmic laser treatment apparatus according to claim 18, wherein
- the characterizing portions are portions having a peak luminance intensity.

20. The ophthalmic laser treatment apparatus according to claim 19, wherein
- the characterizing portions comprise portions corresponding to an inner and outer segment layer and a retinal pigment epithelium layer.

* * * * *